United States Patent [19]

Isobe

[11] Patent Number: 5,107,105
[45] Date of Patent: Apr. 21, 1992

[54] METHOD FOR MEASURING AN UNKNOWN PARAMETER OF A THIN FILM AND APPARATUS THEREFOR

[75] Inventor: Tami Isobe, Yokohama, Japan

[73] Assignee: Ricoh Company, Ltd., Tokyo, Japan

[21] Appl. No.: 610,088

[22] Filed: Nov. 7, 1990

Related U.S. Application Data

[63] Continuation-in-part of Ser. No. 428,822, Oct. 30, 1989, abandoned.

[30] Foreign Application Priority Data

Nov. 2, 1988 [JP] Japan .................. 63-278058
Nov. 7, 1988 [JP] Japan .................. 63-281083

[51] Int. Cl.$^5$ .................................... G02F 1/01
[52] U.S. Cl. .................................... 250/225; 250/560; 356/369
[58] Field of Search .............. 250/560, 225; 356/369, 356/381, 382

[56] References Cited

U.S. PATENT DOCUMENTS

| 4,672,196 | 6/1987 | Canino | 250/225 |
| 4,695,162 | 9/1987 | Itonaga | 356/369 |
| 4,806,776 | 2/1989 | Kley | 250/560 |
| 4,906,844 | 3/1990 | Hall | 250/225 |

FOREIGN PATENT DOCUMENTS 3834948 8/1989 Fed. Rep. of Germany .

OTHER PUBLICATIONS

US-Z. Applied Optics 19, 1980, S. 1031-1032.
NL-Z. Philips Technische Rundschau 35, 1975, S. 70-71.
US-Z. IEEE Transactions on Microwave Theory and Techniques, vol. MTT-23, Jan. 1975, S. 176-177.
US-Z. IBM J. Res. Develop., May 1973, S. 256-262.
GB-Z. J. Phys. E 6, 1973, S. 48-50.
US-Z. Applied Optics 10, 1971, S. 2344-2349.

Primary Examiner—David C. Nelms
Attorney, Agent, or Firm—Cooper & Dunham

[57] ABSTRACT

A method for measuring an unknown parameter, such as a refractive index, absorption coefficient and film thickness of the uppermost layer of a multi-layered film formed on a substrate whose refractive index and absorption coefficient are known, the refractive index, absorption coefficient, and film thickness of the other layer or layers than the uppermost layer on the multi-layered film being known, and at least one of the refractive index $n_1$, absorption coefficient $k_1$ and film thickness $d_1$ of the uppermost layer being unknown, includes the step of measuring the reflectances, the step of specifying the functions containing unknown parameters, and the step of numerically solving the equation.

6 Claims, 4 Drawing Sheets

METHOD FOR MEASURING AN UNKNOWN PARAMETER OF A THIN FILM AND APPARATUS THEREFOR

CROSS-REFERENCE TO RELATED APPLICATION

The present application is a continuation-in-part of application Ser. No. 428,822 field on Oct. 30, 1989, which is abandoned.

BACKGROUND OF THE INVENTION

The present invention relates to a method for measuring an unknown parameter of a thin film, such as a refractive index, absorption coefficient, and film thickness, and more particularly to a method for measuring an unknown parameter, such as a refractive index, absorption coefficient, and film thickness, of the uppermost thin film of a multi-layered film.

The ellipsometry has been known as a noncontact and nondestructive method for measuring the refractive index. This method, however, requires a complicated and huge apparatus.

U.S. Pat. application Ser. Nos. 07/256,911 and 7/453,902, which were invented by the same inventor as that of the present patent application, discloses a novel method for measuring the refractive index of a thin film layer. In this method, P-polarized monochromatic light and S-polarized monochromatic light are made to enter the thin film whose refractive index is to be measured, reflectances for them are measured, and a refractive index of the thin film is mathematically worked out by using the results of the measurements.

The application of the above methods, however, is limited only to the thin film that is transparent to the wavelength of the used light, and further is applicable for a single layer thin film structure alone.

SUMMARY OF THE INVENTION

With the view of overcoming the above problem, the present invention has an object to provide a novel method for measuring an unknown parameter, such as a refractive index, absorption coefficient and film thickness, not only of a single layered film but also of the uppermost layer film of a multi-layered film structure.

The present invention has another object to provide a novel method for measuring a refractive index of the uppermost layer of a multi-layered thin film structure and a single layer thin film structure as well.

According to one aspect of the present invention, there is provided "a method for measuring a refractive index, absorption coefficient and film thickness of the upperost layer of a multi-layered film formed on a substrate whose refractive index and absorption coefficient are known, in which the refractive index, absorption coefficient, and film thickness of the other layer than the uppermost layer of the multi-layered film are known, and the refractive index $n_1$, absorption coefficient $k_1$ and film thickness $d_1$ of the uppermost layer are unknown." In the case of a single layered thin film structure, the single layered thin film is treated as the "uppermost layer" In this case, it is only needed that the refractive index and the absorption coefficient of only the substrate are known.

The method comprises the step of measuring the reflectances, the step of specifying the functions containing unknown parameters, and the step of numerically solving the functions.

The measuring step is to measure "reflectances $Rp(\theta_{oh})$ and $Rs(\theta_{oh})$ ($h=1, 2, ..., j$) for P-polarized monochromatic light and S-polarized monochromatic light, each of which has a wavelength of "$\lambda$", when the P-polarized monochromatic light and S-polarized monochromatic light are incident on the multi-layered films on the substrate at different incident angles $\theta_{01}$, $\theta_{02}, ..., \theta_{oj}$ ($j \geq i$ where "i" indicates the number of unknown values and $i \leq 3$)".

The function specifying step is to specify "the following j equations containing variables of only the refractive index $n_1$, absorption coefficient $k_1$ and film thickness $d_1$ of the uppermost layer, $$4\pi d_1/\lambda = \gamma_1(n_1, k_1)$$
$$4\pi d_1/\lambda = \gamma_2(n_1, k_1)$$
$$\vdots$$
$$4\pi d_1/\lambda = \gamma_j(n_1, k_1)$$

in accordance with Fresnel equations and by using the refractive index and the absorption coefficient of the substrate, the refractive index, the absorption coefficient, and the film thickness of the other layer than the uppermost layer of the multi-layered film, and the measured reflectances $Rp(\theta_{oh})$ and $R_s(\theta_{oh})$, and the incident angles $\theta_{01}, \theta_{02}, ..., \theta_{oj}$".

The numerically solving step is to numerically solve "the equations, thereby to obtain the unknown values of the refractive index $n_1$, the absorption coefficient $k_1$ and the film thickness $d_1$ of the uppermost layer".

With such an arrangement, the present measuring method is capable of accurately and simply measuring a refractive index, an absorption coefficient and a film thickness of the uppermost layer of a multi-layered film and a single layered film as well in a noncontact and nondestructive manner.

According to another aspect of the present invention, there is provided "a method for measuring a refractive index of the uppermost layer of a multi-layered film formed on a substrate whose refractive index and absorption coefficient are known, in which refractive index, absorption coefficient, and film thickness of the other layer than the uppermost layer of the multi-layered film are known, and the uppermost layer is transparent to a measuring monochromatic light without any absorption." In the case of a single layered thin film structure, the single layered thin film is treated as the "uppermost layer".

The method comprises the step of measuring the reflectances, the step of specifying the functions containing only the refractive index $n_1$ as the variable, and the step of numerically solving the functons.

The measuring step is to measure "reflectances for P-polarized monochromatic light and S-polarized monochromatic light, when the P-polarized monochromatic light and S-polarized monochromatic light are incident on the multi-layered films on the substrate at different incident angles".

The function specifying step includes the step of "specifying the right sides $fp(n_1)$ and $fs(n_1)$ in the following equations as functions each containing only a variable "$n_1$" on the basis of the refractive index and the absorption coefficient of the substrate, the refractive index, the absorption coefficient and the film thickness of the other layer than the uppermost layer of the multi-layered film, and the refractive index of an incident medium, the incident angles, the wavelength of each of the monochromatic light, and the reflectances Rp and Rs, $$\cos(2\beta_1 + \delta p) = fp(n_1)$$

$$\cos(2\beta_1 + \delta s) = fs(n_1)$$

where $2\beta hd\ 1$ is a phase change that results from a double traversal of each of the polarized monochromatic lights in the uppermost layer, $\delta p$ and $\delta s$ are phase changes of the P- and S-polarized monochromatic lights respectively at the interface between the uppermost layer and the underlying structure which includes the other layers than the uppermost layer and the substrate, and $n_1$ represents the refractive index of the uppermost layer".

The function specifying step further includes the step of "specifying the right sides $gp(n_1)$ and $gs(n_1)$ in the following equations as functions each containing only a variable "$n_1$" on the basis of the refractive index and the absorption coefficient of the substrate, the refractive index, the absorptlon coefficient and the film thickness of the other layer than the uppermost layer of the multi-layered film, and the wavelength and the incident angle of each of the monochromatic lights".

$$\delta p = gp(n_1)$$

$$\delta s = gs(n_1)$$

The numerically solving step is to stepwise change the refractive index $n_1$ of the uppermost layer as parameters, and numerically solve the following equation for each parameter on the basis of the $fp(n_1)$ and $fs(n_1)$, and $gp(n_1)$ and $gs(n_1)$, thereby to find a value of the refractive index $n_1$ satisfying the following equation and to determine the value of the refractive index $n_1$ as the refractive index $n_1$ of the uppermost layer, $$[\{fp(n_1)\cos(gs(n_1)) - fs(n_1)\cos(gp(n_1))\}/$$

$$\{\sin(gs(n_1))\cos(gp(n_1)) - \cos(gs(n_1))\sin(gp(n_1))\}]^2 +$$

$$[\{fp(n_1)\sin(gs(n_1)) - fs(n_1)\sin(gp(n_1))\}/\{\sin(gs(n_1))\cos(gp(n_1)) -$$

$$\cos(gs(n_1))\sin(gp(n_1))\}]^2 = 1.$$

In specifying the functions $fp(n_1)$, $fs(n_1)$, $gp(n_1)$ and $gs(n_1)$, some optical principles, particularly Fresnel,s formulae are used. The function specifying step and the numerically solving- step are executed by a calculating means, e.g., a computer.

With such an arrangement, the present measuring method is capable of accurately and simply measuring a refractive index of the uppermost layer of a multi-layered film and a single layered film in a noncontact and nondestructive manner.

Other objects, features and advantages of the present invention will be apparent from the following description taken in connection with the accompanying drawings.

DETAILED DESCRIPTION OF THE INVENTION

Before proceeding with the preferred embodiments of the present invention, the principles of the present invention will be described with reference to FIG. 1.

There is described the principle of a method for measuring an unknown parameter, such as a refractive index, absorption coefficient and film thickness of the uppermost layer of the multi-layered film which has more than one film on a substrate whose refractive index and absorption coefficient are known, in which the refractive index, absorption coefficient, and film thickness of the other layer or layers than the uppermost layer of the film structure are known, and at least one of the refractive index $n_1$, absorption coefficient $k_1$ and film thickness $d_1$ of the uppermost-layer are unknown.

Figure 1A:
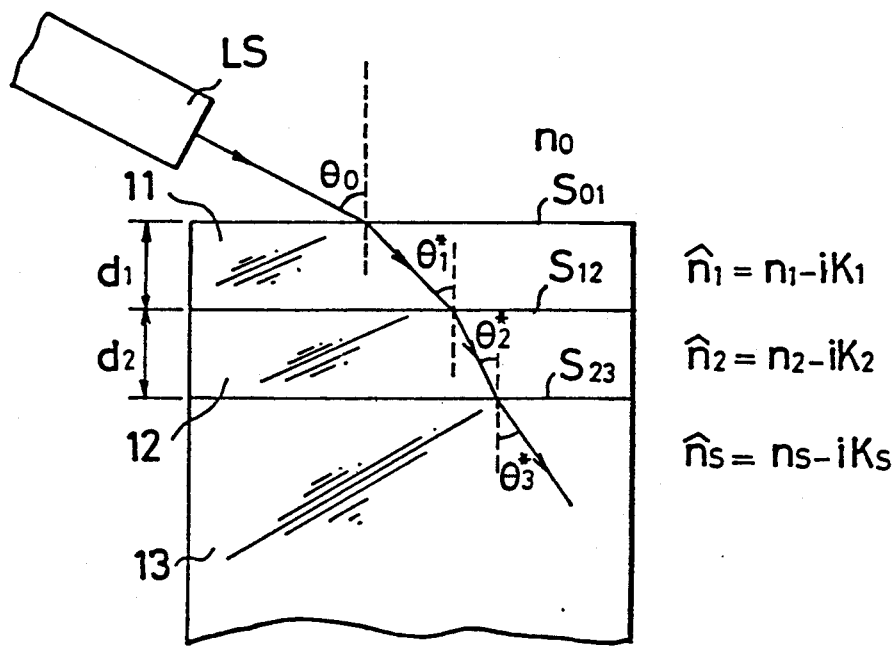
FIGS. 1A and 1B show explanatory diagrams for explaining the principles of the present invention.

In FIG. 1A, LS designates a laser source. A measured film consists of two thin films 11 and 12 on a substrate 13. As shown in FIG. 1A, the film layer 11 is the uppermost layer of the film structure. The refractive index, absorption coefficient and film thickness of the uppermost layer will be measured. It is assumed that the values of the refractive index, absorption coefficient and film thickness of the uppermost layer are unknown.

In the figure, let $S_{01}$ be an interface between an incident medium and the thin film 11, $S_{12}$ be an interface between the thin films 11 and 12, and $S_{23}$ be an interface between the thin film 12 and the substrate 13. Further, let $n_0$, $n_1$, $n_2$ and $n_s$ be respectively the refractive indices of the incident medium, the films 11 and 12, and the substrate 13. Those indices $n_1$, $n_2$ and $n_s$ are given by $$\hat{n}_1 = n_1 - ik_1, \hat{n}_2 = n_2 - ik_2, \hat{n}_s = n_s - ik_s \qquad (1)$$

In each equation, the imaginary part represents the absorption coefficient. Normally, 1 of the refractive index of air may be used for the refractive index $n_0$. In the figure, $d_1$ and $d_2$ represents the thickness of the thin films 11 and 12; $\theta$, an incident angle of the incident light on the thin film 11; $\theta_1^*$, $\theta_2^*$, and $\theta_3^*$, the angles of refraction at the interfaces $S_{01}$, $S_{12}$ and $S_{23}$, respectively.

Figure 1B:
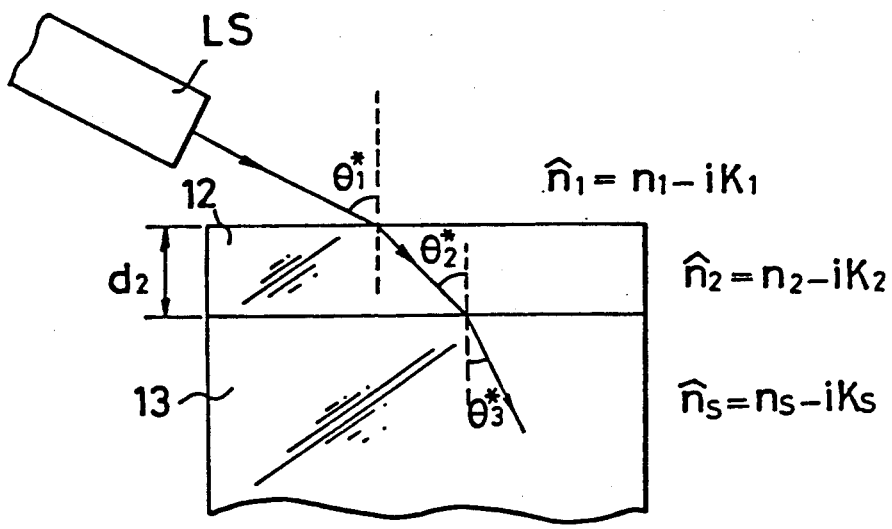

Of those parameters as mentioned above, $n_0$, $n_2$, $n_s$ and $d_2$ are known. The incident angle $\theta_o$ and a wavelength of the incident light emitted from the laser source LS can be preselected as measuring conditions. In FIG. 1B, there is the film 12 layered on the substrate 13. The film 12 and the substrate 13 have the same refractive indices and thickness as those of the film 12 and the substrate 13 in FIG. 1A. And the refractive index of the incident medium is $n_1$ which is the same as the refractive index of the film 11 in FIG. 1A.

As shown in FIG. 1B, when monochromatic light is incident on the film, from the laser source LS at an angle of $\theta_1$, the amplitude reflectance of the reflected light can be expressed as follows:

$$r_s' = [r_{12s} + r_{23s} \cdot \exp\{2i\beta_2^*\}]/ \qquad (2\text{-}1)$$
$$[1 + r_{12s} \cdot r_{23s} \cdot \exp\{2i\beta_2^*\}]$$

$$r_p' = [r_{12p} + r_{23p} \cdot \exp\{2i\beta_2^*\}]/ \qquad (2\text{-}2)$$
$$[1 + r_{12p} \cdot r_{23p} \cdot \exp\{2i\beta_2^*\}]$$

where, s indicates s-polarized light, p indicates p-polarized light, $r_{12}$ represents Fresnel's reflection coefficient at the interface $S_{12}$, and $r_{23}$ represents Fresnel's reflection coefficient at the interface $S_{23}$. Those reflection coefficients may be expressed in terms of the incident angle $\theta^*_1$, and the refractive angle $\theta^*_2$, and $\theta^*_3$ in the following way, $$r_{12P} = (\hat{n}_2\cos\theta_1^* - \hat{n}_1\cos\theta_2^*)/ \qquad (3\text{-}1)$$
$$(\hat{n}_2\cos\theta_1^* + \hat{n}_1\cos\theta_2^*)$$

$$r_{12S} = (\hat{n}_1\cos\theta_1^* - \hat{n}_2\cos\theta_2^*)/ \qquad (3\text{-}2)$$
$$(\hat{n}_1\cos\theta_1^* + \hat{n}_2\cos\theta_2^*)$$

$$r_{23P} = (\hat{n}_s\cos\theta_2^* - \hat{n}_2\cos\theta_3^*)/ \qquad (3\text{-}3)$$
$$(\hat{n}_s\cos\theta_2^* + \hat{n}_2\cos\theta_3^*)$$

$$r_{23S} = (\hat{n}_2\cos\theta_2^* - \hat{n}_s\cos\theta_3^*)/ \qquad (3\text{-}4)$$
$$(\hat{n}_2\cos\theta_2^* + \hat{n}_s\cos\theta_3^*)$$

In the equations (2-1) and (2-2), $2\beta^*_2$ represents a phase change that results from a double traversal of each of the polarized monochromatic lights in the film 12, and it can be mathematically described by $$2\beta^*_2 = 4\pi n_2 d_2(\cos\theta^*_2)/\gamma \qquad (4)$$

where
$\lambda$ = wavelength of the incident light,
$d_2$ = thickness of the film,
$\theta^*_2$ = angle of refraction, and
$n_2$ = refractive index of the film 12.

Returning to FIG. 1A, in the case of the double-layered film which consists of the film 11 and the film 12, the amplitude reflectances at the interface $S_{12}$ are equivalent to the amplitude reflectances, $r_s'$ and $r_p'$ in the equations (2-1) and (2-2). Therefore, the amplitude reflectances $r_s$ and $r_p$ of the double-layered film can be written as follows:

$$r_S = [r_{01S} + r_S' \cdot \exp\{2i\beta_1^*\}]/ \qquad (5\text{-}1)$$
$$[1 + r_{01S} + r_S' \cdot \exp\{2i\beta_1^*\}]$$

-continued $$r_P = [r_{01P} + r_P' \cdot \exp\{2i\beta_1^*\}]/ \qquad (5\text{-}2)$$
$$[1 + r_{01P} \cdot r_P' \cdot \exp\{2i\beta_1^*\}]$$

where S and P are the same as defined in equations (2-1) and (2-2), $r_{01}$ is the Fresnel,s reflection coefficient at the itterface $s_{01}$, and is given by $$r_{01P} = (\hat{n}_1\cos\theta_0 - n_0\cos\theta_1^*)/ \qquad (5\text{-}3)$$
$$(\hat{n}_1\cos\theta_0 + n_0\cos\theta_1^*)$$

$$r_{01S} = (n_0\cos\theta_0 - \hat{n}_1\cos\theta_1^*)/ \qquad (5\text{-}4)$$
$$(n_0\cos\theta_0 + \hat{n}_1\cos\theta_1^*)$$

A phase change $2\beta^*_1$ that results from a double traversal of each of the polarized monochromatic lights in the film 11 is given by $$2\beta^*_1 = 4\pi\hat{n}_1 d_1(\cos\theta^*_1)/\gamma \qquad (6)$$

Furthermore, if the measured film has more than 3 layered films on the substrate, viz., the other films are located between the thin film 12 and the substrate 13 in FIG. 1A, the amplitude reflectance cn be obtained by repeating the above sequence of procedure. Generally, the equations (5-1) and (5-2) are directly applicable to the amplitude reflectances of the uppermost layer of the multi-layered thin films formed on a substrate, if the amplitude reflectances at the interface between the uppermost layer and the incident medium are $r_{01p}$ and $r_{01s}$, and if the amplitude reflectances at the interface between the uppermost layer and the underlying structure which includes the other layers than the uppermost layer and the substrate are $r_p'$ and $r_s'$.

The amplitude reflectances $r_{01s}$, $r_{01p}$, $r_s'$ and $r_p'$ are generally expressed by complex values, and can be written as $$r_{01S} = \rho_{01S} \cdot \exp(i\phi_{01S}) \qquad (7\text{-}1)$$

$$r_{01P} = \rho_{01P} \cdot \exp(i\phi_{01P}) \qquad (7\text{-}2)$$

$$r_S' = \rho_S \cdot \exp\{i\delta_S\} \qquad (7\text{-}3)$$

$$r_P' = \rho_P \cdot \exp\{i\delta_P\} \qquad (7\text{-}4)$$

Further, the phase change $2\beta^*_1$ is also expressed in terms of the complex value, and is written as follows $$2\beta^*_1 = \alpha(u_1 + iv_1) \qquad (7\text{-}5)$$

where $\alpha$, $u$, and $v_1$ are expressed as follows:
$\alpha = 4\pi d_1/\lambda$.

$$2u_1 = n_1^2 - k_1^2 - n_0^2\sin^2\theta_0 + \qquad (7\text{-}6)$$
$$\sqrt{(n_1^2 - k_1^2 - n_0^2\sin^2\theta_0)^2 + 4n_1^2k_1^2}$$

$$2v_1 = -(n_1^2 - k_1^2 - n_0^2\sin^2\theta_0) + \qquad (7\text{-}7)$$
$$\sqrt{(n_1^2 - k_1^2 - n_0^2\sin^2\theta_0)^2 + 4n_1^2k_1^2}$$

Substituting the relations (7-1) to (7-5) into the equations (5-1) and (5-2), we have the following equations (8-1) and (8-2).

$$r_S = [\rho_{01S} \cdot \exp(i\phi_{01S}) + \rho_S \cdot \exp(-\nu_1 a) \cdot \qquad (8\text{-}1)$$
$$\exp\{i(\delta_S + u_1 a)\}]/[1 + \rho_{01S} \cdot \delta_S \cdot$$
$$\exp(-\nu_1 a) \cdot \exp\{i(\phi_{01S} + \delta_S u_1 a)\}]$$

$$r_P = [\rho_{01S} \cdot \exp(i\phi_{01S}) + \rho_P \cdot \exp(-\nu_1 a) \cdot \qquad (8\text{-}2)$$
$$\exp\{i(\delta_P + u_1 a)\}]/[1 + \rho_{01S} \cdot \delta_S \cdot$$
$$\exp(-\nu_1 a) \cdot \exp\{i(\phi_{01P} + \delta_S + u_1 a)\}]$$

Assuming that $\exp(-\nu_1 a) = \rho$ and $u_1 a = \theta$, the reflectances can be written as follows.

$$R_P = |r_P|^2 = \qquad (9\text{-}1)$$
$$[\rho_{01P}^2 + \rho_P^2 \rho^2 + 2\rho_{01P}\rho_P\rho\cos(\delta_P - \phi_{01P} + \theta)]/$$
$$[1 + \rho_{01P}^2 + \rho_P^2\rho^2 + 2\rho_{01P}\rho_P\rho\cos(\phi_{01P} + \delta_P + \theta)]$$

$$R_S = |r_S|^2 = \qquad (9\text{-}2)$$
$$[\rho_{01S}^2 + \rho_S^2\rho^2 + 2\rho_{01S}\rho_S\rho\cos(\delta_S - \phi_{01S} + \theta)]/$$
$$[1 + \rho_{01S}^2 + \rho_S^2\rho^2 + 2\rho_{01S}\rho_S\rho\cos(\phi_{01S} + \delta_S + \phi)]$$

The equations (9-1) and (9-2) can be rewritten into $$A_P\cos\theta - B_P\sin\theta = C_P \qquad (10\text{-}1)$$

$$A_S\cos\theta - B_S\sin\theta = C_S \qquad (10\text{-}2)$$

where
$A_S = R_S\cos(\phi_{01S} + \delta_S) - \cos(\delta_S - \delta_{01S})$
$A_P = R_P\cos(\phi_{01P} + \delta_P) - \cos(\delta_P - \delta_{01P})$
$B_S = R_S\sin(\phi_{01S} + \delta_S) - \sin(\delta_S - \delta_{01S})$
$B_P = R_P\sin(\phi_{01P} + \delta_S) - \sin(\delta_S - \delta_{01P})$ Solving the equations (10-1) and (10-2) for $\sin\theta$ and $\cos\theta$, we have $$\sin\theta = (C_P A_S - A_P C_S)/(A_P B_S - B_P A_S) \qquad (11\text{-}1)$$

$$\cos\theta = (C_P B_S - B_P C_S)/(A_P B_S - B_P A_S) \qquad (11\text{-}2)$$

By utilizing the identical equation $\sin^2\theta + \cos^2\theta = 1$, we have $$C_P^2(A_S^2 + B_S^2) + C_S^2(A_P^2 + B_P^2) = \qquad (12)$$
$$2C_P C_S(A_P A_S + B_P B_S) = (A_P B_S - B_P A_S)^2$$

Rearranging the equation (12) for $\rho$, we have following quadratic equation $$a(\theta) = \rho_{01S}^2 \rho_S^2 \cdot \rho_P^4(1 - R_P\rho_{01P}^2)^2(A_S^2 + B_S^2) +$$
$$\rho_{01P}^2 \rho_P^2 \rho_S^4(1 - R_S\rho_{01S}^2)^2(A_P^2 + B_P^2) -$$
$$2\rho_{01S}\rho_S^3\rho_{01P}\rho_P^3(1 - R_P\rho_{01P}^2)$$
$$(1 - R_S\rho_{01S}^2)(A_P A_S + B_P B_S)$$

$$b(\theta) = 2\rho_{01S}^2\rho_S^2\rho_P^2(\rho_{01P}^2 - R_P)(1 - R_P\rho_{01P}^2)(A_S^2 + B_S^2) +$$
$$2\rho_{01P}^2\rho_P^2\rho_S^2(\rho_{01S}^2 - R_S)(1 - R_S\rho_{01S}^2)(A_P^2 + B_P^2) -$$
$$2\rho_{01S}^2\rho_S\rho_{01P}^2\rho_P$$
$$\{(\rho_{01P}^2 - R_P)\rho_S^2(1 - R_S\rho_{01S}^2) + (\rho_{01S}^2 - R_S)$$
$$\rho_P^2(1 - R_P\rho_{01P}^2)\}(A_P A_S + B_P B_S) -$$
$$4\rho_{01S}^2\rho_S^2\rho_{01P}^2\rho_P^2(A_P A_S + B_P B_S)^2$$

$$c(\theta) = \rho_{01S}^2\rho_S^2(\rho_{01P}^2 - R_P)^2(A_S^2 + B_S^2) +$$
$$\rho_{01P}^2\rho_P^2(\rho_{01S}^2 - R_S)^2(A_P^2 + B_P^2) -$$

-continued
$$2\rho_{01S}\rho_S\rho_{01P}\rho_P(\rho_{01S}^2 - R_P)$$
$$(\rho_{01S}^2 - R_S)(A_P A_S + B_P B_S)$$

Solving the quadratic equation (13) for $\rho$, we find $$\rho = \{-b(\theta) \pm \sqrt{b^2(\theta) - 4a(\theta)b(\theta)}\,\}/2a(\theta) \qquad (14)$$

Since $\rho = \exp(-\nu_1 a)$, when substituting it into the equation (14) and then have $$a = -(1/\nu_1)\ln[-b(\theta) \pm \sqrt{b^2(\theta) - 4a(\theta)b(\theta)}\,/2a(\theta)] \qquad (15)$$

Hence, $a$ can be expressed by the following function $\gamma$, $$a = \gamma(\lambda, \theta_0, n_0, n_1, \ldots, n_m, k_1, k_2, \ldots, k_m, d_2, \ldots, d_m, n_S, k_S, R_P, R_S). \qquad (16)$$

$\gamma$ is the function of the wavelength $\lambda$ of the monochromatic light, the angle of incidence $\theta_0$, refractive index $n_0$ of the incident medium (normally $n_0 = 1$), the refractive index and absorption coefficient $n_s$ and $k_s$ of the substrate, the refractive indexed $n_1$ to $b_m$ and absorption coefficients $k_1$ to $k_m$ of m thin layers on the substrate, the thickness $d_2$ to $d_m$, and reflectances $R_p$ and $R_s$.

As mentioned above, $a$ is defined as $4\pi d_1/\lambda$.

In the relation (16), of those factors defining $\lambda$, $\theta_o$, $n_0$, $n_s$, $k_s$, $n_2$ to $n_m$, $k_2$ to $k_m$, $d_2$ to $d_m$ are known, and the reflectances $R_P$ and $R_S$ can be obtained by their measurements. Accordingly, after the reflectances $R_P$ and $R_s$ are measured, the following equation containing unknown parameters $n_1$, $k_1$ and $d_1$ can be obtained $$4\pi d_1/\lambda = \gamma(n_1, k_1) \qquad (17)$$

The function can automatically speedily be calculated by a computer if the calculating process is programmed and loaded into the computer.

The equation (17) contains three unknown parameters. To specify these unknown parameters, it is necessary to set up at least three equations (17), and to solve them as simultaneous equations. The simultaneous equations may set up in such a manner that the incident angle is varied and the resultant reflectances are measured.

Where the incident angle is varied, the reflectance generally varies. Accordingly, the parameters $\theta$, $R_p$ and $R_s$ are varied and finally the equations equivalent to the equation (17) can be obtained.

As seen from the foregoing description, where of those parameters, the refractive index $n_1$, absorption coefficient $k_1$ and film thickness $d_1$ of the uppermost layer of a multi-layered film structure, the number of unknown parameters is "i" ($i \leq 3$), the necessary number of equations is at least "i".

Reflectances $R_p(\theta_{oh})$ and $R_s(\theta_{oh})$ (h = 1, 2, ..., j) for P-polarized monochromatic light and S-polarized monochromatic light, each of which has a wavelength of "$a$", are measured under the condition that the P-polarized monochromatic light and S-polarized monochromatic light are made to enter the multi-layered films on the substrate at different incident angles $\theta_{01}$, $\theta_{02}$, ..., $\theta_{oj}$ ($j \geq i$ where "i" indicates the number of unknown values and $i \leq 3$).

The following j equations, which contain variables of only the refractive index $n_1$, absorption coefficient $k_1$ and film thickness $d_1$ of the uppermost layer, are set up $$4\pi d_1/\lambda = \gamma_1(n_1,k_1) \quad (17\text{-}1)$$
$$4\pi d_1/\lambda = \gamma_2(n_1,k_1) \quad (17\text{-}2)$$
$$\vdots$$
$$4\pi d_1/\lambda = \gamma_j(n_1,k_1) \quad (17\text{-}j)$$

Hereinafter a set of the equations (17-1) to (17-j) is represented as $$4\pi d_1/\lambda = \gamma k(n_1, k_1) \ (k=1,2,\ldots, j)$$

In accordance with Fresnel equations and by using the refractive index and absorption coefficient of the substrate, the refractive index, absorption coefficient, and film thickness of the other layer or layers than the uppermost layer of the film structure, and the measured reflectances $R_p(\theta_{oh})$ and $R_s(\theta_{oh})$, and the incident angles $\theta_{01}, \theta_{02}, \ldots, \theta_{oj}$, the equations are solved thereby to obtain the unknown values of the refractive index $n_1$, absorption coefficient $k_1$ and film thickness $d_1$ of the uppermost layer.

Many programs for solving the group of equations as the simultaneous equations by the numerical calculation process, have been developed.

The principle of a method for measuring a refractive index of the uppermost layer of multi-layered film which has more than one film on a substrate whose refractive index and absorption coefficient are known, the refractive index, absorption coefficient, and film thickness of the other layer or layers than the uppermost layer of the film structure are known, and the uppermost layer is transparent to a measuring monochromatic light without any absorption, will be described.

For the description, FIGS. 1A and 1B that have been used for the description of the above-mentioned measuring method will be used.

In this case, the uppermost layer 11 is a thin film that is transparent to the S- and P-polarized monochromatic lights, and a refractive index of the uppermost layer will be measured.

In this case, the uppermost layer 11 is transparent, and hence $\theta^*_1$ shown in FIGS. 1A and 1B is replaced by $\theta_1$ which is not complex.

In the figure, let $n_0$, $n_1$, $n_2$, and $n_s$ be respectively the indices of the incident medium, the films 11 and 12, and the substrate 13. Those complex indices $\hat{n}_2$ and $\hat{n}_s$ are given by $$\hat{n}_2 = n_2 - ik_2, \hat{n}_s = n_s - ik_s \quad (18)$$

In each equation, the imaginary part in the right side represents the absorption coefficient. In the figure, $\theta_1$, $\theta^*_2$, and $\theta^*_3$ respectively represent the angles of refraction at the interfaces $s_{01}$, $n_{12}$ and $n_{23}$, respectively.

Of those parameters as mentioned above, $n_0$, $n_2$, $n_s$ and $d_2$ are known. The incident angle $\theta_0$ and a wavelength of the incident light or laser beam emitted from the laser source LS can be preselected as measuring conditions.

In FIG. 1B, there is the film 12 layered on the substrate 13. The film 12 and the substrate 13, have the same refractive indices and thickness as those of the film 12 and the substrate 13 in FIG. 1A. And the refractive index of the incident medium is $n_1$ which is the same as the refractive index of the film 11 in FIG. 1A.

As shown in FIG. 1B, when monochromatic light is incident on the film, from the laser source LS at an angle of $\theta_1$, the amplitude reflectance of the reflected light can be expressed by the equation (2). In the equation (2), the amplitude reflectance $r_{12}$ and $r_{23}$ may be expressed in terms of the incident angle $\theta_1$, and the refractive angle $\theta_2$, and $\theta_3$ in the following way, $$r_{12P} = (n_2\cos\theta_1 - n_1\cos\theta_2^*)/(n_2\cos\theta_1^* + n_1\cos\theta_2^*) \quad (19\text{-}1)$$

$$r_{12S} = (n_1\cos\theta_1 - n_2\cos\theta_2^*)/(n_1\cos\theta_1 + n_2\cos\theta_2^*) \quad (19\text{-}2)$$

$$r_{23P} = (n_3\cos\theta_2^* - n_2\cos\theta_3^*)/(n_3\cos\theta_2^* + n_2\cos\theta_3^*) \quad (19\text{-}3)$$

$$r_{23S} = (n_2\cos\theta_2^* - n_3\cos\theta_3^*)/(n_2\cos\theta_2^* + n_3\cos\theta_3^*) \quad (19\text{-}4)$$

Returning to FIG. 1A, in the case of the double-layered film which consists of the film 11 and the film 12, the amplitude reflectances at the interface $S_{12}$ are equivalent to the amplitude reflectances $r'_s$ and $r'_p$ in the equations (2-1) and (2-2). Therefore, the amplitude reflectances $r_s$ and $r_m$ of the double-layered film written as follows:

$$r_S = [r_{01S} + r_S' \cdot \exp\{2i\beta_1\}]/[1 + r_{01S} + r_S' \cdot \exp\{2i\beta_1\}] \quad (20\text{-}1)$$

$$r_P = [r_{01P} + r_P' \cdot \exp\{2i\beta_1\}]/[1 + r_{01P} \cdot r_P' \cdot \exp\{2i\beta_1\}] \quad (20\text{-}2)$$

where $r_{01}$ is the Fresnel's reflection coefficient at the interface $S_{01}$, and is given by $$r_{01P} = (n_1\cos\theta_0 - n_0\cos\theta_1)/(n_1\cos\theta_0 + n_0\cos\theta_1) \quad (21\text{-}3)$$

$$r_{01S} = (n_0\cos\theta_0 - n_1\cos\theta_1)/(n_0\cos\theta_0 + n_1\cos\theta_1) \quad (21\text{-}4)$$

A phase change $2\beta_1$ that results from a double traversal of each of the polarized monochromatic lights in the film 11 is given by $$2\beta_1 = 4\pi n_1 d_1(\cos\theta_1)/\lambda \quad (22)$$

Furthermore, if the measured film has more than 3 layered films on the substrate 13, viz., the other films are located between the thin film 12 and the substrate 13 in FIG. 1A, the amplitude reflectance can be obtained by repeating the above sequence of procedure. Generally, the equations (20-1) and (20-2) are directly applicable to the amplitude reflectances of the multi-layered film formed on a substrate, if amplitude reflectances at the interface between the uppermost layer and the incident medium are $r_{01S}$ and $r_{01P}$, and if the amplitude reflectances at the interface between the uppermost layer and the underlying structure which includes the other layers than the uppermost layer and the substrate are $r'_s$.

The amplitude reflectances $r'_s$ and $r'_p$ are generally expressed by the complex values, and can be written as follows.

$$r'_s = \rho_S \cdot \exp\{i\delta_s\} \tag{23-1}$$

$$r'_p = \rho_P \cdot \exp\{i\delta_p\} \tag{23-2}$$

Substituting the equations (23-1) and (23-2) into the equations (20-1) and (20-2), we have $$r_S = [r_{01S} + \rho_S \cdot \exp\{i(2\beta_1 + \delta_S)\}] / \tag{24-1}$$
$$[1 + r_{01S} \cdot \rho_S \cdot \exp\{i(2\beta_1 + \delta_S)\}]$$

$$r_P = [r_{01P} + \rho_P \cdot \exp\{i(2\beta_1 + \delta_P)\}] / \tag{24-2}$$
$$[1 + r_{01P} \cdot \rho_P \cdot \exp\{i(2\beta_1 + \delta_P)\}]$$

The reflectances $R_P$ and $R_S$ are given by $$R_P = |r_P|^2 = [r_{01P}^2 + \rho_P^2 + 2r_{01P}\rho_P\cos(2\beta_1 + \delta_P)] / \tag{25}$$
$$[1 + r_{01P}^2\rho_P^2 + 2r_{01P}\rho_P\cos(2\beta_1 + \delta_P)]$$

$$R_S = |r_S|^2 = [r_{01S}^2 + \rho_S^2 + 2r_{01S}\rho_S\cos(2\beta_1 + \delta_S)] / \tag{26}$$
$$[1 + r_{01S}^2\rho_S^2 + 2r_{01S}\rho_S\cos(2\beta_1 + \delta_S)]$$

Solving the equations (25) and (26) for $\cos(2\beta_1 + \delta_p)$, $\cos(2\beta_1 + \delta_s)$,
We have $$\cos(2\beta_1 + \delta_p) = [r_{01P}^2 + \rho_P^2 - R_P(1 + r_{01P}^2 \cdot \rho_P^2)] / \tag{27}$$
$$[2r_{01P} \cdot \rho_P(R_P - 1)]$$

$$\cos(2\beta_1 + \delta_S) = [r_{01S}^2 + \rho_S^2 - R_S(1 + r_{01S}^2 \cdot \rho_S^2)] / \tag{28}$$
$$[2r_{01S} \cdot \rho_S(R_S - 1)]$$

Let the right side of the equation (27) be defined as the function $f_p$, then the equation (27) can be written $$\cos(2\beta_1 + \delta_p) = [r_{01P}^2 + \rho_P^2 - R_P(1 + r_{01P}^2 \cdot \rho_P^2)] / \tag{27'}$$
$$[2r_{01P} \cdot \rho_P(R_P - 1)] = f_P$$

Let the right side of the equation (28) be defined as the function $f_s$, then the equation (28) can be written $$\cos(2\beta_1 + \delta_S) = [r_{01S}^2 + \rho_S^2 - R_S(1 + r_{01S}^2 \cdot \rho_S^2)] / \tag{28'}$$
$$[2r_{01S} \cdot \rho_S(R_S - 1)] = f_S$$

$\delta_s$, $\delta_p$, $\rho_s$ and $\rho_p$ can be described by a function of the refractive index $n_1$ of the uppermost layer of the film structure, if the refractive index (including absorption coefficient) of the substrate, the refractive index of the incident medium, and the refractive index and the film thickness (includign absorption coefficient) of the other film or films other than the uppermost layer are know. In the case of the double layered films as shown in FIG. aA, $\delta_s$, $\delta_p$, $\rho_p$, $\rho_s$ can be expressed as follows:

$$\tan\delta_P = [\rho_{23P}(1 - \rho_{12P}^2)\sin(u_2\alpha + \phi_{23P}) + \tag{29}$$
$$\rho_{12P}(\exp\{v_2\alpha\} - \rho_{23P}^2\exp\{-v_2\alpha\})\sin\phi_{12P}] /$$
$$[\rho_{23P}(1 + \rho_{12P}^2)\cos(u_2\alpha + \phi_{23P}) +$$
$$\rho_{12P}(\exp\{v_2\alpha\} - \rho_{23P}^2\exp\{-v_2\alpha\})\cos\phi_{12P}] = g_P$$

$$\tan\delta_S = [\rho_{23S}(1 - \rho_{12S}^2)\sin(u_2\alpha + \phi_{23S}) + \tag{30}$$
$$\rho_{12S}(\exp\{v_2\alpha\} - \rho_{23S}^2\exp\{-v_2\alpha\})\sin\phi_{12S}] /$$
$$[\rho_{23S}(1 + \rho_{12S}^2)\cos(u_2\alpha + \phi_{23S}) +$$
$$\rho_{12S}(\exp\{v_2\alpha\} - \rho_{23S}^2\exp\{-v_2\alpha\})\cos\phi_{12S}] = g_S$$

where $g_p$ and $g_s$ are used in the same way as in the equations (27,) and (28,).

$$|\rho_P|^2 = [\rho_{12P}^2 + \rho_{23P}^2\exp\{-2v_2\alpha\} + \tag{31}$$
$$2\rho_{12P}\rho_{23P}\exp\{-v_2\alpha\}\cos(\phi_{23P} - \phi_{12P} + u_2\alpha)] /$$
$$[1 + \rho_{12P}^2\rho_{23P}^2\exp\{-2v_2\alpha\} +$$
$$2\rho_{12P}\rho_{23P}\exp\{-v_2\alpha\}\cos(\phi_{12P} - \phi_{23P} + u_2\alpha)]$$

$$|\rho_S|^2 = [\rho_{12S}^2 + \rho_{23S}^2\exp\{-2v_2\alpha\} + \tag{32}$$
$$2\rho_{12S}\rho_{23S}\exp\{-v_2\alpha\}\cos(\phi_{23S} - \phi_{12S} + u_2\alpha)] /$$
$$[1 + \rho_{12S}^2\rho_{23S}^2\exp\{-2v_2\alpha\} +$$
$$2\rho_{12S}\rho_{23S}\exp\{-v_2\alpha\}\cos(\phi_{12S} - \phi_{23S} + u_2\alpha)]$$

In the above equations (29) to (32), $\hat{n}\cos\theta^*_2$, $\hat{n}_3\cos\theta^*_3$, and $r_{12S}$ are defined as follows.

$$\hat{n}_2\cos\theta_2^* = u_2 + iv_2, \quad \hat{n}_3\cos\theta_3^* = u_3 + iv_3$$

$$r_{12P} = \rho_{12P}\exp\{i\phi_{12P}\}, \quad r_{12S} = \rho_{12S} \cdot \exp\{i\phi_{12S}\},$$

$$r_{23P} = \rho_{23P}\exp\{i\phi_{23P}\}, \quad r_{23S} = \rho_{23S} \cdot \exp\{i\phi_{23S}\},$$

and $\alpha = 4\pi d_2/\lambda$

By using the equations (19-1) to (19-4), $\rho_{12P}$, $\rho_{12S}$, $\rho_{23P}$, $\rho_{23S}$, $\phi_{23S}$ can be written as $$\rho_{(j-1)jP}^2 = \{(q1 \cdot q3 + q2 \cdot q4)^2 + (q2 \cdot q3 - q1 \cdot q4)^2\} / \tag{33}$$
$$(q3^2 + q4^2)^2$$

$$\rho_{(j-1)jS} = \{(u_{j-1}^2 - u_j^2 + v_{j-1}^2 - v_j^2)^2 + 4(u_jv_{j-1} - u_{j-1}v_j)^2\} / \{(u_{j-1} + u_j)^2 + (v_{j-1} + v_j)^2\}^2 \tag{34}$$

$$\tan\phi_{(j-1)jP} = (q2 \cdot q3 - q1 \cdot q4)/(q1 \cdot q3 + q2 \cdot q4) \tag{35}$$

$$\tan\phi_{(j-1)jS} = 2(u_jv_{j-1} - u_{j-1}v_j)/[u_{j-1}^2 - u_j^2 + v_{j-1}^2 - v_j^2] \tag{36}$$

$$\tan\phi_{23P} = [q2 \cdot q3 - q1 \cdot q4]/[q1 \cdot q3 + q2 \cdot q4] \tag{37}$$

where $j = 2, 3$.
In the above equations, $$q1 = (n_j^2 - k_j^2)u_{j-1} + 2n_jk_jv_{j-1} - (n_{j-1}^2 - k_{j-1}^2)u_j - 2n_{j-1}k_{j-1}v_j$$

$$q2 = (n_j^2 - k_j^2)v_{j-1} + 2n_jk_ju_{j-1} - (n_{j-1}^2 - k_{j-1}^2)v_j + 2n_{j-1}k_{j-1}u_j$$

$$q3 = (n_j^2 - k_j^2)u_{j-1} + 2n_jk_jv_{j-1} + (n_{j-1}^2 - k_{j-1}^2)u_j +$$

-continued $$q^4 = (n_j^2 - k_j^2)v_{j-1} + 2n_jk_ju_{j-1}^2 + (n_{j-1}^2 - k_{j-1}^2)v_j - 2n_{j-1}k_{j-1}u_j$$

$$2u_j^2 = n_j^2 - k_j^2 - n_0^2\sin^2\theta_0 + \sqrt{(n_j^2 - k_j^2 - n_0^2\sin^2\theta_0)^2 + 4n_j^2k_j^2}$$

$$2v_j^2 = -(n_j^2 - k_j^2 - n_0^2\sin^2\theta_0) + \sqrt{(n_j^2 - k_j^2 - n_0^2\sin^2\theta_0)^2 + 4n_j^2k_j^2}$$

Meanwhile, consider the quantitiers $\cos(2\beta_1+\delta_p)$, $\cos(2\beta_1+\delta_s)$. From the relationd (27) and (28), those quantities can be expressed by $$\cos(2\beta_1 + \delta_P) = f_P(\lambda, \theta_0, n_0, n_1, n_2, n_3, d_2, R_P) \quad (38)$$

$$\cos(2\beta_1 + \delta_S) = f_S(\lambda, \theta_0, n_0, n_1, n_2, n_3, d_2, R_S) \quad (39)$$

From the relations (29) and (30), $\delta_P$ and $\delta_S$ can also be written as $$\delta_P = g_P(\lambda, \theta_0, n_0, n_1, n_2, n_3, d_2) \quad (40)$$

$$\delta_S = g_S(\lambda, \theta_0, n_0, n_1, n_2, n_3, d_2) \quad (41)$$

The function can automatically speedily be calculated by a computer if the calculating processes are programmed and loaded into the computer.

Of those parameters, $n_1$, $n_2$, $n_s$ and $d_1$ are known. is also known because the frequency of the laser beam generated by the laser source LS is known. Further, $\theta_o$ is known because it is one of the incident angles, and preset before measurement.

If known parameters are substituted in the functions fp, fs, gp and gs, those functions contain only "$n_1$" as the unknown parameter. Developing the left sides of the equation (38) and (39) into trigonometric polynomials by
using the trigonometric formula, and solving the polynomials for $\sin 2\beta_1$, $\cos 2\beta_1$, we have $$\sin 2\beta_1 = \{f_P(n_1)\cos\delta_S - f_S(n_1)\cos\delta_P\}/\{\sin\delta_S\cos\delta_P - \sin\delta_P\cos\delta_S\} \quad (42)$$

$$\cos 2\beta_1 = \{f_P(n_1)\sin\delta_S - f_S(n_1)\sin\delta_P\}/\{\sin\delta_S\cos\delta_P - \sin\delta_P\cos\delta_S\} \quad (43)$$

$\sin 2\beta_1$ and $\cos 2\beta_1$, satisfy the identical equation $\sin^2 2\beta_1+\cos^2 2\beta_1=1$.

Substituting the equations (42) and (43) into the left side of the identical equation, it can be rewritten into $$[\{f_P(n_1)\cos(g_S(n_1)) - f_S(n_1)\cos(g_P(n_1))\}/\{\sin(g_S(n_1))\cos(g_P(n_1)) - \cos(g_S(n_1))\sin(g_P(n_1))\}]^2 + [\{f_P(n_1)\sin(g_S(n_1)) - f_S(n_1)\sin(g_P(n_1))\}/\{\sin(g_S(n_1))\cos(g_P(n_1)) - \cos(g_S(n_1))\sin(g_P(n_1))\}]^2 = 1.$$

The equation (44) contains only $n_1$ as the variable. The $n_1$ which satisfies the equation (44) is the correct value of the refractive index of the uppermost layer of the film structure.

To solve numerically the equation (44), many programs have been developed.

While the present invention has been described using the multi-layered film structure having the wo thin films 11 and 12 formed on the substrate 13, it is evident that the present invention is applicable for another multi-layered film structure having three or more thin films. In other words, the equation (44) is applicable for measuring refractive index of a thin film of the multi-layered film structure having three or more thin films.

Provided that the refractive index $n_s$ (including the absorption coefficient) of the substrate, the refractive indices $n_2$, ..., $n_m$ (including the absorption coefficient) (m = integer of more than 3) and film thicknesses $d_2$, ..., $d_m$ of the thin film layers other than the uppermost layer are known, $$\cos(2\beta_1+\delta_p), \cos(2\beta_1+\delta_s), \delta_s, \delta_p$$

can be treated as the functions each containing only the refractive index $n_1$ as the variable as follows.

$$\cos(2\beta_1 + \delta_P) = f_P(n_1), \cos(2\beta_1 + \delta_S) = f_S(n_1)$$
$$\delta_P = g_P(n_1), \delta_S = g_S(n_1)$$

Thus, the equation (44) can be obtained and the correct value of the refractive index $n_1$ can be obtained by solving that equation.

EXAMPLES

Examples to perform the method for measuring a refractive index, absorption coefficient and film thickness of a thin film according to the present invention, that is based on the first principle as mentioned above, will be described.

Figure 2:
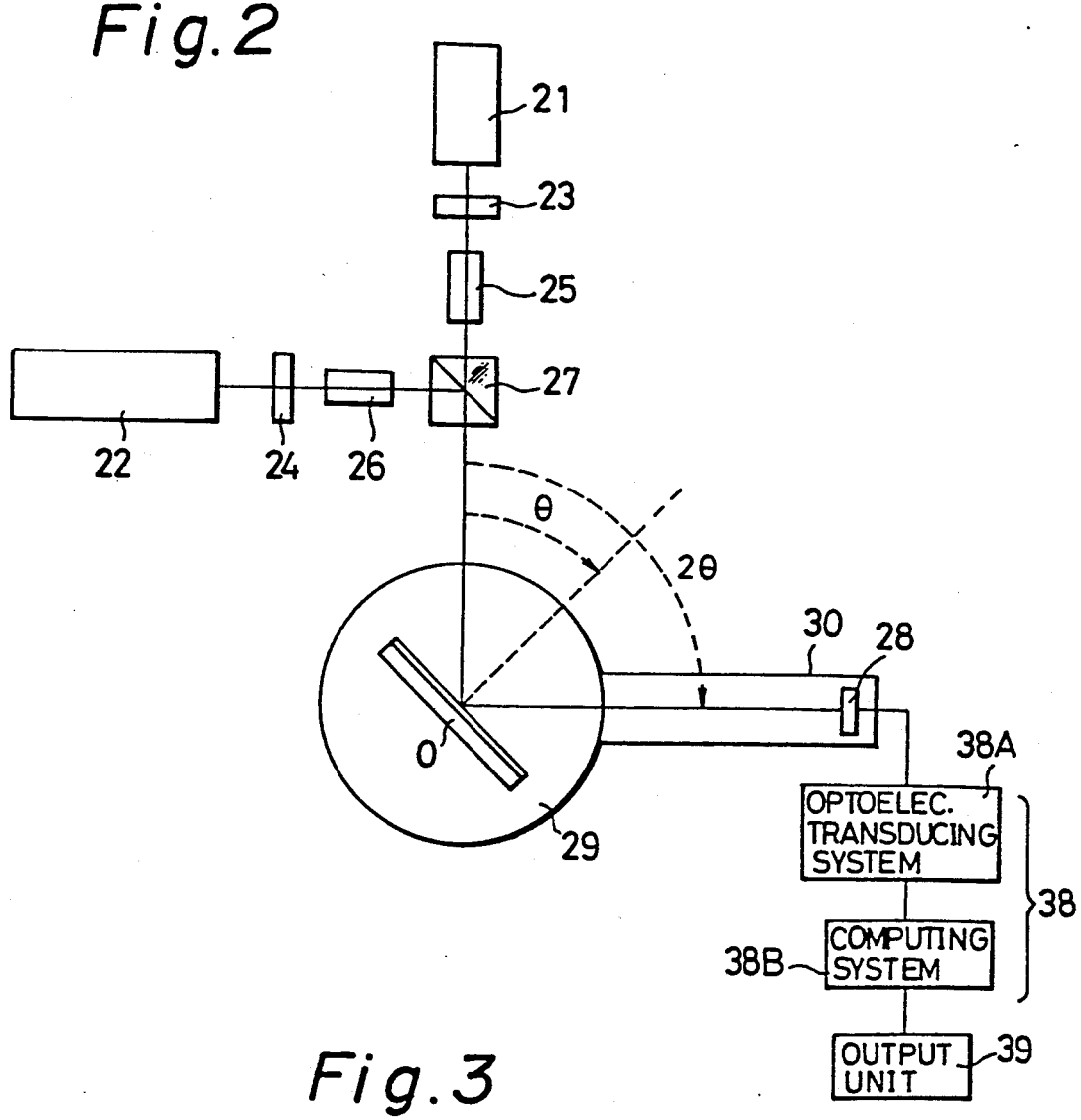
FIG. 2 shows in schematic and block form a measuring system by which a method for measuring an unknown parameter, such as a refractive index, absorption coefficient and film thickness, of the uppermost layer of a thin film structure according to the present invention is performed.

FIG. 2 shows a first measuring system for performing the method for measuring refractive index, absorption coefficient or film thickness of a thin film according to the present invention.

Light sources 21 and 22 are installed. Each of the light sources is an He-Ne laser whose output is stable. A laser beam generated by the laser has a wavelength of 6328Å. Polarizers 25 and 26 are respectively installed in the paths of the laser beams emitted from the light sources 21 and 22. The polarizers 25 and 26 receive and polarize the laser beams, and produce S- and P-polarized monochromatic beams, respectively. Shutters 23 and 24 are provided; the shutter 23 is located between the light source 21 and the polarizer 25, and the shutter 24, between the light source 22 and the polarizer 26. Through the action of the shutters 23 and 24, the S- or P-polarized light or laser beam is selectively applied to a polarized beam splitter 27 with a high optical extinction ratio. The splitter 27 lead the received S-or P-polarized laser beam to an object O to be measured or a sample.

The sample O is placed on a turn table 29. A photo detector 28 is mounted to the distal end of an arm 30. The turn table 29 and the arm 30 constitute a $(\theta-2\theta)$ rotation system. In the rotation system, when the arm 30 is rotated by $2\theta$ in a direction, the turn table 29 rotates by $\theta$ in the same direction. With this system, an angle of the incident light or laser beam to the sample O placed on the turn table 20 may be varied in the range of 0 to 90° by means of the arm 30.

The output signal of the photo detector 28 on the arm 30 is led to a data processing system 38. The data processing system 38 is made up of an optoelectric transducing system 38A, and a-computing circuit 38B for computing the output aata signal of the optoelectric transducing system. The computing system 38B may be a computer and sets up a set of the equations and solves the equations through a numerical calculation process. The results of the calculation are applied to an output unit 39.

In this instance, the sample was a film structure in which an SiN film layered on a substrate of Si. Plasma CVD process was used for forming the SiN film on the substrate.

Measurement was made of the refractive index $n_1$, absorption coefficient $k_1$ and film thickness $d_1$ of the thin film of SiN.

For the measurement, the sample was set to the measuring system of FIG. 2. The angle $\theta$ of the incident laser beam was set at three angles; $\theta_{01}, =30, \theta_{02} =45°$, and $\theta_{03} =60°$. The S-polarized laser beam was applied to the sample O at these different angles. The reflectances were measured. Similarly, the P-polarized laser beam was applied to the same, and the reflectances were measured for the P-polarized laser beam at those different incident angles. The results of the measurements were as follows:

$$R_P(\theta_{01} = 30°) = 0.03432, R_P(\theta_{02} = 45°) = 0.01430,$$
$$R_P(\theta_{03} = 60°) = 0.00318$$
$$R_S(\theta_{01} = 30°) = 0.08119, R_S(\theta_{02} = 45°) = 0.13599,$$
$$R_S(\theta_{03} = 60°) = 0.25276$$

By using the reflectances, the above-mentioned equation can be set up,

In the equation, $\gamma_1=\gamma_2=\gamma_3$ must hold for the true values of the $n_1$ and $k_1$.

Accordingly, the refractive index $n_1$ (or the absorption coefficient $k_1$) is set at an appropriate value. The absorption coefficient $k_1$ (or the refractive index $n_1$) is varied as a parameter to check whether or not there is a value of the $k_1$ (or $n_1$) which satisfies the relation $\gamma_1=\gamma_2=\gamma_3$. If such a value of the k; (or $n_1$) is not found, the $n_1$ (or $k_1$) is set at another value, and the same process is repeated. This process may be programmed and be executed by a computer. If the values of the $n_1$ and $k_1$ that satisfy the relation $\gamma_1=\gamma_2=\gamma_3$ are found, those values are put into the right side of the above equation, and the thickness $d_1$ of thin film can be obtained.

Figure 3:
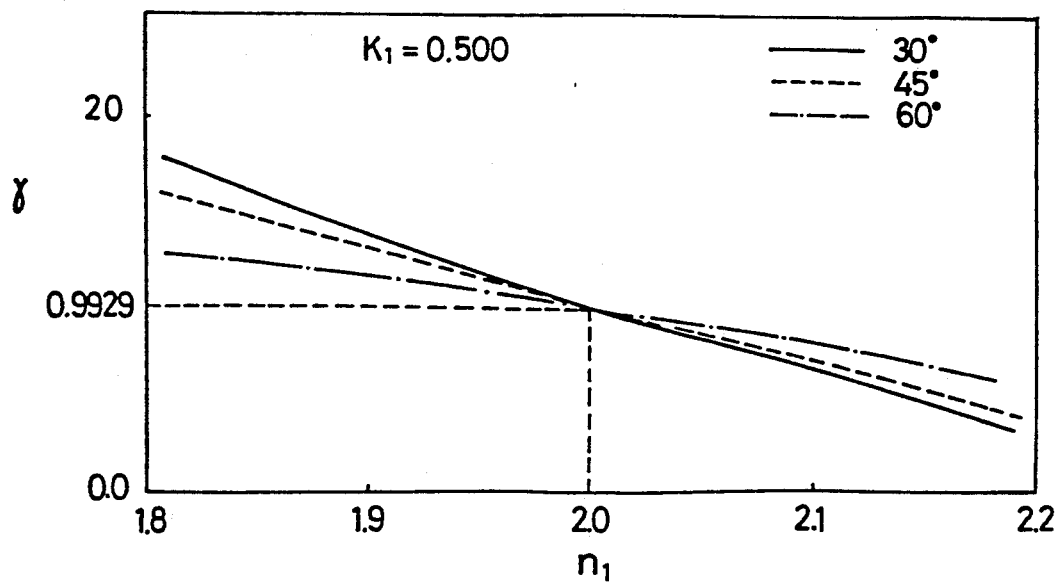
FIG. 3 is a graph showing the results obtained when the measuring method based on a first principle of the present invention is performed by the measuring system of FIG. 2.

In the instant embodiment, for calculating $\gamma_1$, $\gamma_2$, and $\gamma_3$, the $k_1$ was set at 0.400, and the value of the n; was varied from 1.800 to 2.200. The try failed to found the value of the $n_1$ which satisfies the $\gamma_1=\gamma_2=\gamma_3$. Then, the value of the $k_1$ is incrementally shifted from 0.400, and the same process was repeated. At 0.500 of the $k_1$, $\gamma_1$, $\gamma_2$, $\gamma_3$ varied with respect to the $n_1$, as shown in FIG. 3. As seen, when $n_1=2.000, \gamma_1=\gamma_2=\gamma_3=0.9929$ was satisfied.

From the above fact, it can be understood that the refractive index $n_1$ of the SiN thin film is 2.000, and the absorption coefficient $k_1$ is 0.500. The thickness $d_1$ of the film can be worked out by putting 0.9929 in the right side of the equation and putting 6328Å in the wavelength Å. The figure of the film thickness $d_1$ thus worked out is 500Å.

Figure 4:
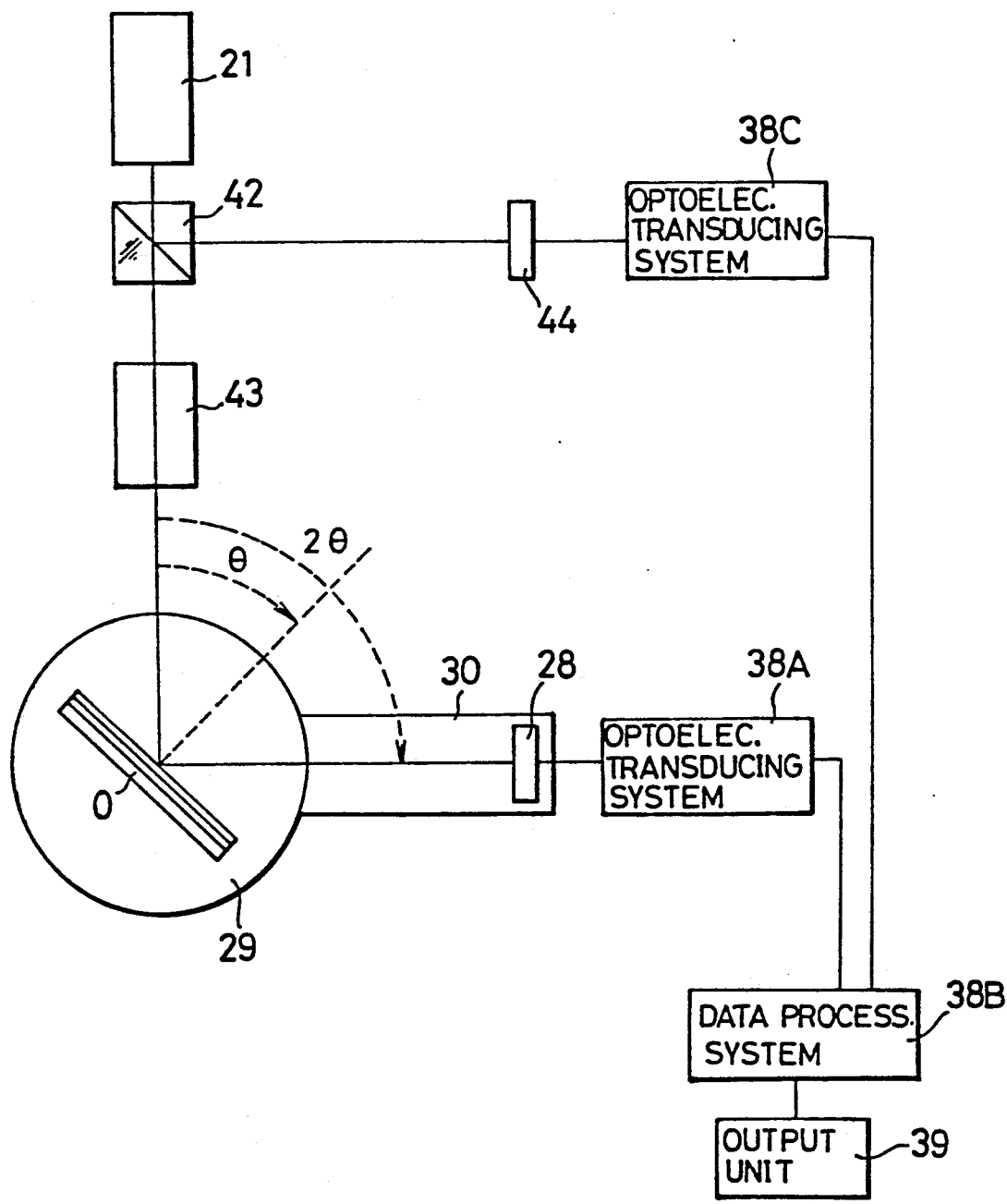
FIG. 4 shows in schematic and block form another measuring system by which the measuring method according to the present invention is performed.

Turning now to FIG. 4, there is shown another measuring system for performing the method for measuring refractive index, absorption coefficient or film thickness of a thin film according to the present invention. In FIG. 4, like reference symbols are used for designating like or equivalent portions in FIG. 2, for simplicity.

In the testing system, a laser beam of the wavelength of 6328Å is emitted from an He-Ne laser 21 and applied to a beam splitter 42. The splitter 42 splits the received laser beam into two beams, first and second laser beams. The first laser beam is applied to an optoelectric transducing system 38C. The system 38C transduces the first laser beam into an electric data signal, and transfers it to a-data processing system 38B.

The second laser beam enters a polarizer 43. The polarizer 43 polarizes the second laser beam into an S-or P-polarized laser beam, and applies it to a sample O.

The sample O was a multi-layered film structure. The film structure was formed in a manner that an $SiO_2$ film was deposited on an Si substrate by thermal oxidation process, and an SiN film was further formed on the $SiO_2$ film by plasma CVD process. The refractive index of the substrate was 3.858–0.018i. The refractive index of the $SiO_2$ film was 1.460 and the thickness thereof was 5000Å. In the measurement, the absorption coefficient $k_1$ was known, $k_1 =0.500$, and the refractive index nI and the film thickness $d_1$ were unknown.

The incident angles were: $\theta_{01}=30°$ and $\theta_{02}=60°$. The reflectances for the S- and P-polarized laser beams were measured at the respective incident angles. The results of the measurement of the reflectances were:

$$R_p(\theta_{01}=30°)=0.22609, R_p(\theta_{02}=60°)=0.00313,$$
$$R_s(\theta_{01}=30°)=0.33770, R_s(\theta_{02}=60°)=0.30120$$

By using the above results, the following equation can be set up $$4\pi d_1/\lambda = \gamma k(n_1) \ (K=1,2)$$

In the above equation, "k" is known, and hence the variable in the right side of the equation is only "n". For the true value of the $n_1$, $\gamma_1=\gamma_2$ must hold.

Figure 5:
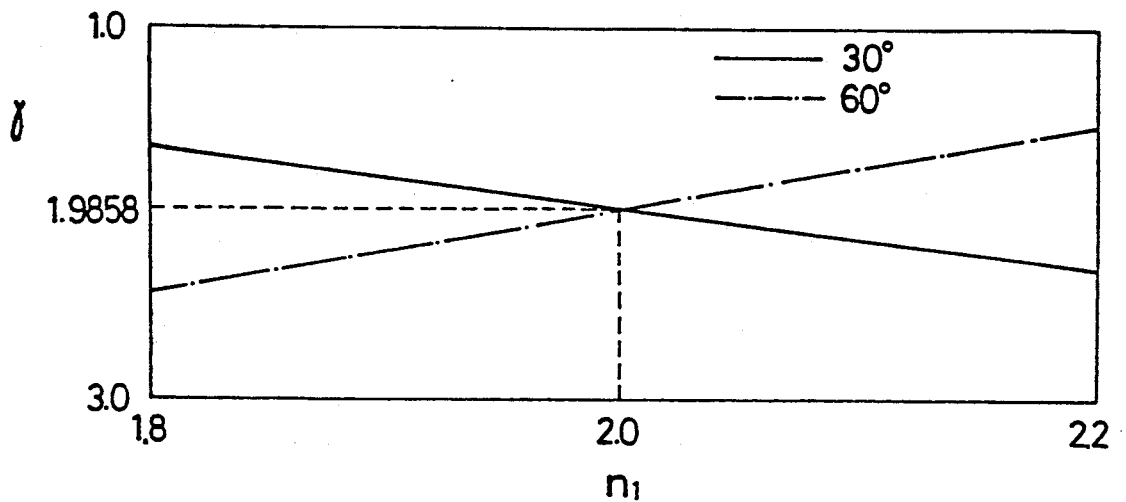
FIG. 5 is a graph showing the results obtained when the measuring method based on the first principle is performed by the measuring system of FIG. 4.

In this instance, $\gamma_1$ and $\gamma_2$ were calculated for the values of the $n_1$ between 1.800 and 2.200. The values of $\gamma_1$ and $\gamma_2$ vs. the nI were plotted as shown in FIG. 5. As seen from the graph, $\gamma_1 =\gamma_2 = 1.9858$ at $n_1 =2.000$.

Accordingly, $4\pi d_1 \lambda=1.9858$ and $\gamma=6328$Å, and hence $d_1 =1000$Å.

In this way, the measurement showed that the refractive index of the SiN thin film was 2.0 and the film thickness was 1000Å.

Description to follow is an example to execute the method for measuring a refractive index of a thin film according to the present invention that is based on the second principle as mentioned above.

The measuring system shown in FIG. 2 was used as a measuring system for performing the example.

In this example, the step to specify the functions fp, fs, gp and gs of the refractive index $n_1$ and the step to solve the equation (44) to specify the $n_1$, are processed by the data processing system 38.

A sample used was a multi-layered thin film structure in which an SiN fil-m of the refractive index 2.0–0.1i is deposited on an Si substrate of the refractive index 3.858–0.018i by plasma CVD process, the deposited SiN film was 1000Å, and an $SiO_2$ film was further formed on the SiN film by sputtering process.

The refractive index of the $SiO_2$, or the uppermost layer, was measured.

The sample O was set on the turn table table 29 of the measuring system of FIG. 2, and an angle $\theta$ of the S-and P-polarized laser beams incident on the thin film structure was 45°.

The S- and P-polarized monochromatic laser beams were selectively applied to the sample O by operating the shutters 43A and 43B. The amounts of the reflected laser beams were measured by the photo detector 28 and the reflectances $R_p$ and $R_s$ were calculated as follows:

$R_s = 0.12228$ and $R_p = 0.03190$.

These figures of the reflectances $R_s$ and $R_p$, the refractive index $n_s = 3.858 - 0.018i$ of the substrate, the refractive index $n_2 = 2.0 - 0.1i$ of the SiN thin film, the film thickness $d_2 = 1000$Å, and the wavelength $\lambda = 6328$Å, and the incident angle $\theta_o = 45°$ were applied to the equation (43). To solve the equation (43), the value of the parameter $n$; was changed from 1.3 to 1.6 in increments of 0.001 (this increment figure may appropriately be selected). For each value of the parameter, the left side of the equation (43) was calculated. The results of the calculations were plotted as shown in FIG. 6.

Figure 6:
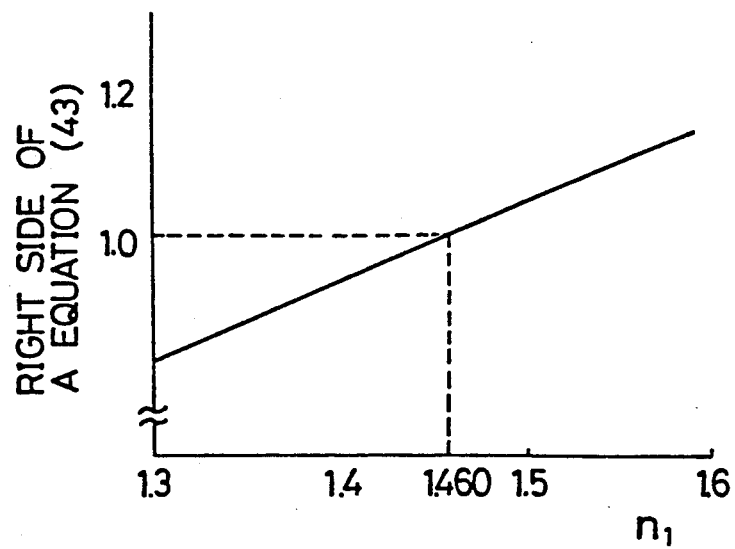
FIG. 6 is a graph showing the results obtained when the measuring method based on a second principle of the present invention is performed by the measuring system of FIG. 2.

As seen from FIG. 6, when $n_1 = 1.460$, the equation (44) holds. Consequently, the refractive index of the SiO2 thin film was found to be 1.460.

Many widely different embodiments of the present invention may be constructed without departing from the spirit and scope of the present invention. It should be understood that the present invention is not limited to the specific embodiments described in this specification, except as defined in the appended claims.

What is claimed is:

1. A method for measuring refractive index, absorption coefficient and film thickness of the uppermost layer of a multi-layered film formed on a substrate whose refractive index and absorption coefficient are known, the refractive index, absorption coefficient, and film thickness of the other layer than the uppermost layer of said film being known, and at least one of the refractive index $n_1$, absorption coefficient $k_1$ and film thickness $d_1$ of said uppermost layer being unknown, said method comprising the steps of:

measuring reflectances $R_p(\theta_o)$ and $R_s(\theta_{oh})$ (h = 1,2, ..., j) for P-polarized monochromatic light a and S-polarized monochromatic light, each of which has a wavelength of $\lambda$, when said the P-polarized monochromatic light and said S-polarized monochromatic light are incident on said multi-layered films on said substrate at different incident angles $\theta_{01}, \theta_{02}, ..., \theta_{oj}$ j (j $\geqq$ i where i represents the number of unknown values and i $\leqq 3$);

specifying the right side of the following equation (1) as a function containing variables of said refractive index $n_1$, said absorption coefficient $k_1$, and said reflectances $Rp(\theta_{oh})$ and $Rs(\theta_{oh})$ on the basis of said wavelength $\lambda$, a refractive index $n_o$ of an incident medium, said refractive index $n_s$ and said absorption coefficient $k_s$ of said substrate, said refractive indexes n2, n3, ..., $n_m$, said absorption coefficient $k_2, k_3, ..., k_m$, and said film thicknesses $d_2, d_3, ..., d_m$ of the other layers than said uppermost layer, $$4\pi d_1/\lambda = \gamma[\lambda, n_0, n_1, n_2, \ldots, n_m, k_1, k_2, \ldots, k_m, d_2, d_3, \ldots, d_m, n_s, k_s, Rp(\theta_{oh}), Rs(\theta_{oh})] \quad (1)$$

where $d_1$ represents a film thickness of said uppermost layer, and the others are the same as defined above, to thereby obtain the following equation (2), $$4 \times d_1 \pi = \lambda[n_1, K_1, Rp(\theta oh), Rs(\theta oh),] \quad (2)$$

specifying sequentially the right side of the above equation (2) as functions $\gamma_1, \gamma_2, ..., \gamma_j$ containing respectively variables of $n_1$ and $k_1$ and corresponding respectively to said incident angles $\theta_{01}, \theta_{02}, ..., \theta_{0j}$ on the basis of said measured reflectances $Rp(\theta_{oh})$ and $Rs(\theta oh)$ to obtain the following equations (3), (4), ..., (j+2)

$$4\pi d_1/\lambda = r_1[n_1, k_1] \quad (3)$$
$$4\pi d_1/\lambda = r_2[n_1, k_1] \quad (4)$$
$$\vdots$$
$$4\pi d_1/\lambda = r_j[n_1, k_1] \quad (j+2)$$

solving numerically said obtained equations (3), (4), ..., (j+2) for unknown values of said refractive index $n_1$, said absorption coefficient $k_1$ and said film thickness $d_1$ of said uppermost layer.

2. An apparatus for measuring optical constants and thickness of a thin film structure comprising:

polarized light beam emitting means for emitting alternately a P-polarized light beam and an S-polarized light beam;

a supporting means arranged on an optical path of said emitted P-polarized light beam and said emitted S-polarized light beam for supporting said thin film structure in such a manner that a multi-layered film of said supported thin film structure can receive said emitted P-polarized light beam and said emitted S-polarized light beam at different incident angles $\theta_{oh}$ (h = 1, 2, ..., j, j => i where i represents the number of unknown value and i < 3);

a photodetector means arranged on an optical path of said P-polarized light beam and said S-polarized light beam which are reflected from said multi-layered films for detecting said reflected P-polarized light beam and said reflected S-polarized light beam, for transducing intensities of said detected P-polarized light beam and said detected S-polarized light beam into corresponding electric signals, and for outputting said transduced electric signals; and a data processing means electrically connected to said photodetector means and adapted to determine reflectances $Rp(\theta_{oh})$ and $Rs(\theta_{oh})$ (h = 1, 2, ..., j) of said P-polarized light beam and said S-polarized light beam which are made to enter said multi-layered films at said different incident angles $\theta$oh (h = 1, 2, ..., j) on the basis of said outputted electric signals, to specify the right side of the following equation (1) as a function containing variables of a refractive index n and an absorption coefficient k of an uppermost layer of said multi-layered film formed on a substrate of said thin film structure and said determined reflectances $Rp(\theta oh)$ and $Rs(\theta oh)$ on the basis of a wavelength $\lambda$ of said emitted P-polarized and S-polarized light beams, a refractive index $n_0$ of an incident medium, a refractive index $n_s$ and an absorption coefficient $k_s$ of said substrate, refractive indexes n2, n3, ..., nm, absorption coefficient k2, k3, ..., $k_m$, and film thicknesses $d_2, d_3, ..., d_m$ of the other layers than said uppermost layer, $$4\pi d_1/\lambda = \gamma[\lambda, n_0, n_1, n_2, \ldots, n_m, k_1, k_2, \ldots, k_m, d_2, d_3, \ldots, d_m, n_s, k_s, Rp(\theta_{oh}), Rs(\theta_{oh})] \quad (1)$$

where $d_1$ represents a film thickness of said uppermost layer and the others are the same as defined above, to thereby obtain the following equation (2), to specify sequentially the right side of the above equation (2) as functions $\gamma_1, \gamma_2, ..., \gamma_j$ containing respectively variables of $n_1$ and $k_1$ and corresponding respectively to said incident angles $\theta_{01}, \theta_2, ..., \theta_{0j}$ on the basis of said determined reflectances Rp($\theta$oh) and Rs($\theta_{oh}$) to thereby obtain the following equations (3), (4), ..., (j+2)

$$4\pi d_1/\lambda = \gamma_1[n_1, k_1] \quad (3)$$
$$4\pi d_1/\lambda = \gamma_2[n_1, k_1] \quad (4)$$
$$\vdots$$
$$4\pi d_1/\lambda = \gamma_j[n_1, k_1] \quad (j+2)$$

and to solve numerically said obtained equations (3), (4), ..., (j+2) for unknown values of said refractive index $n_1$, said absorption coefficient $k_1$ and said film thickness $d_1$ of said uppermost layer.

3. An apparatus according to claim 2, in which said polarized light beam emitting means comprises:
   a first light source for generating a first laser beam;
   a second light source arranged in a direction of crossing perpendicularly a first optical path of said generated first laser beam for generating a second laser beam in such a manner as to cross perpendicularly said generated first laser beam;
   a first polarizer arranged on said first optical path between said first light source and a osition where said first optical path crosses perpendicularly a second optical path of said generated second laser beam for producing a S-polarized light beam from said generated first laser beam;
   a second polarizer arranged on said second optical path between said second light source and said position for producing a P-polarized light beam from said generated second laser beam;
   a directing means arranged at said position for directing said produced S-polarized light beam towards said thin film structure while linearly propagating said produced S-polarized light beam along said first optical path, and for directing said produced P-polarized light beam in a direction where said directed first S-polarized light beam travels;
   a first shutting means arranged on said first optical path between said first light source and said first polarizer for shutting off said generated first laser beam to thereby inhibit an arrival of said S-polarized light beam at said thin film structure; and
   a second shutting means arranged on said second optical path between said second light source and said second polarizer for shutting off said generated second laser beam to thereby inhibit an arrival of said P-polarized light beam at said thin film structure.

4. A method for measuring refractive index of the uppermost layer of a multi-layered film formed on a substrate whose refractive index and absorption coefficient are known, refractive indices, absorption coefficients, and film thicknesses of the other layer than the uppermost layer of said film structure being known, and said uppermost layer is transparent to a measuring monochromatic light without any absorption, said method comprising the steps of:
   measuring reflectances for P-polarized monochromatic light and S-polarized monochromatic light, when the P-polarized monochromatic light and S-polarized monochromatic light are incident on the multi-layered film on said substrate at different incident angles;
   specifying the right side fp($n_1$) and fs($n_1$) in the following equations (1) and (2) as functions each containing only a variable of said refractive index $n_1$ of said uppermost layer on the basis of said refractive index and said absorption coefficient of said substrate, said refractive index, said absorption coefficient and said film thickness of said other layer than said uppermost layer, a refractive index of an incident medium, said incident angles, the wavelength of each of said monochromatic light, said measured reflectance $R_p$ of said P-polarized monochromatic light and said measured reflectance Rs of said S-polarized monochromatic light $$\cos(2\beta+\delta) = fr(n_i) \quad (1)$$
$$\cos(2\beta_1+\delta_s) = f_s(n_1) \quad (2)$$

where $2\beta_1$ is a phase change that results from a double traversal of each of said S-polarized monochromatic light and said P-polarized monochromatic light in said uppermost layer, $\delta_p$ and $\delta_s$ are phase changes of said P-polarized monochromatic light and said S-polarized monochromatic light respectively at an interface between said uppermost layer and an underlying structure which includes the other layers than said uppermost layer and said substrate, and $n_1$ represents said refractive index of said uppermost layer;
specifying the right sides gp($n_1$) and gs($bn_1$) in the following equations (3) and (4) as functions each containing only a variable of said refractive index n; of said uppermost layer on the basis of said refractive index and said absorption coefficient of said substrate, said refractive index, said absorption coefficient and said film thickness of said other layer than said uppermost layer, a refractive index of an incident medium, the wavelength of each of said polarized monochromatic lights, and said incident angle of each of said polarized monochromatic lights, $$\delta_P = gp(n_1) \quad (3)$$
$$\delta_s = gs(n_1) \quad (4)$$

where $\delta_p$, $\delta_s$ and $n_1$ are the same as in the equations (1) and (2), respectively;
calculating the respective right sides fp($n_1$), fs($n_1$), gp($n_1$) and gs($n_1$) in the above equations (1), (2), (3) and (4) while changing stepwise a value of $n_1$, calculating the left side in the following equation (5) on the basis of eespective values of said calculated right sides fr($n_1$), fs($n_1$), gp($n_1$) and gs($n_1$), determining a value of $n_1$ satisfying the following equation (5), and specifying said determined value of $n_1$ as said refractive index of said uppermost layer, $$\{(fp(n_1)\cos(gs(n_1))) - fs(n_1)\cos(gp(n_1)))/ \quad (5)$$
$$\{\sin(gs(n_1))\cos(gp(n_1)) - \cos(gs(n_1))\sin(gp(n_1)))\}^2 +$$
$$[(fp(n_1)\sin(gs(n_1))) - fs(n_1)\sin(gp(n_1)))/$$
$$\{\sin(gs(n_1))\cos(gp(n_1)) - \cos(gs(n_1))\sin(gp(n_1)))\}^2 = 1.$$

5. An apparatus for measuring optical constants and thickness of a thin film structure comprising:
   polarized light beam emitting means for emitting alternately a P-polarized light beam and an S-polarized light beam;
   a supporting means arranged on an optical path of said emitted P-polarized light beam and said emitted S-polarized light beam for supporting said thin film structure in such a manner that a multi-layered film of said supported thin film structure can receive said emitted P-polarized light beam and said emitted S-polarized light beam at different incident angles;

a photodetector means arranged on an optical path of said P-polarized light beam and said S-polarized light beam which are reflected from said multi-layered film for detecting said reflected P-polarized light beam and said reflected S-polarized light beam, for transducing intensities of said detected P-polarized light beam and said detected S-polarized light beam into corresponding electric signals, and for outputting said transduced electric signals; and a data processing means electrically connected to said photodetector means and adapted to determine a reflectance $R_p$ of said detected P-polarized light beam and a reflectance $R_s$ of said detected S-polarized light beam on the basis of said outputted electric signals, to specify the right side $fp(n_1)$ and $fs(n_1)$ in the following equation (1) and (2) as functions each containing only a variable of a refractive index $n_1$ of said uppermost layer on the basis of a refractive index and an absorption coefficient of a substrate of said thin film structure, a refractive index, an absorption coefficient and a film thickness of the other layer than said uppermost layer of said multi-layered film, a refractive index of an incident medium, said incident angle, the wavelength of each of said P-polarized and S-polarized light beams, beam and said determined reflectance Rs of said S-polarized light beam $$\cos(2\beta_1 + \delta_s) = fp(n_1) \qquad (1)$$

$$\cos(2\beta_1 + \delta_s) = fs(n_1) \qquad (2)$$

where $2\beta_1$ is a phase change that results from a double traversal of each of said S-polarized light beam and said P-polarized light beam in said uppermost layer, $\delta_s$ and $\delta_p$ are phase changes of said S-polarized light beam and said P-polarized light beam respectively at an interface between said uppermost layer and an underlying structure which includes the other layers than said uppermost layer and said substrate, and $n_1$ represents said refractive index of said uppermost layer, to specify the right sides $gp(n_1)$ and $gs(n_1)$ in the following equations (3) and (4) as functions each containing only a variable of said refractive index $n_1$ of said uppermost layer on the basis of said refractive index and said absorption coefficient of said substrate, said refractive index, said absorption coefficient and said film thickness of said other layer than said uppermost layer of said multi-layered film, a refractive index of an incident medium, the wavelength of each of said P-polarized and S-polarized light beams, and said incident angle of each of said P-polarized and S-polarized light beams, $$\delta_p = gp(n_1) \qquad (3)$$

$$\delta_s = gs(n_1) \qquad (4)$$

where $\delta_p$, $\delta_s$, and $n_1$ are the same as defined in the equations (1) and (2), respectively to calculate the respective right sides $f(n_1)$, $fs(n_1)$, $g(n_1)$ and $gs(n_1)$ in the above equations (1), (2), (3) and (4) while changing stepwise a value of $n_1$, to calculate the left side in the following equation (5) on the basis of respective values of said calculated right sides $fp(n_1)$, $fs(n_1)$, $gp(n_1)$ and $gs(n_1)$, to determine a value of $n_1$ satisfying the following equation (5), and to specify said determined value of $n_1$ as said refractive index of said uppermost layer, $$[\{fp(n_1)\cos(gs(n_1)) - fs(n_1)\cos(gp(n_1))\}/ \qquad (5)$$
$$\{\sin(gs(n_1))\cos(gp(n_1)) - \cos(gs(n_1))\sin(gp(n_1))\}]^2 +$$
$$[\{fp(n_1)\sin(gs(n_1)) - fs(n_1)\sin(gp(n_1))\}/$$
$$\{\sin(gs(n_1))\cos(gp(n_1)) - \cos(gs(n_1))\sin(gp(n_1))\}]^2 = 1.$$

6. An apparatus according to claim 5, in which said polarized light beam emitting means comprises:

a first light source for generating a first laser beam;

a second light source arranged in a direction of crossing perpendicularly a first optical path of said generated first laser beam for generating a second laser beam in such a manner as to cross perpendicularly said generated first laser beam;

a first polarizer arranged on said first optical path between said first light source and a position where said first optical path crosses perpendicularly a second optical path of said generated second laser beam for producing an S-polarized light beam from said generated first laser beam;

a second polarizer arranged on said second optical path between said second light source and said position for producing a P-polarized light beam from said generated second laser beam;

a directing means arranged at said position for directing said produced S-polarized light beam towards said thin film structure while linearly propagating said produced S-polarized light beam along said first optical path, and for directing said produced P-polarized light beam in a direction where said directed S-polarized light beam travels;

a first shutting means arranged on said first optical path between said first light source and said first polarizer for shutting off said generated laser beam to thereby inhibit an arrival of said S-polarized light beam at said thin film structure; and a second shutting means arranged on said second optical path between said second light source and said second polarizer for shutting off said generated laser beam to thereby inhibit an arrival of said P-polarized light beam at said thin film structure.

* * * * *